(12) United States Patent
Kaneshige

(10) Patent No.: US 6,527,737 B2
(45) Date of Patent: Mar. 4, 2003

(54) INDWELLING URETHRA CATHETER

(76) Inventor: Tatsuo Kaneshige, 428-7, Gumisawa-cho, Totsuka-ku, Yokohama-shi, Kanagawa (JP)

( * ) Notice: Subject to any disclaimer, the term of this patent is extended or adjusted under 35 U.S.C. 154(b) by 0 days.

(21) Appl. No.: 09/767,711

(22) Filed: Jan. 24, 2001

(65) Prior Publication Data

US 2001/0025169 A1 Sep. 27, 2001

(30) Foreign Application Priority Data

Jan. 24, 2000 (JP) ........................................ 2000-014811

(51) Int. Cl.[7] ...................... A61M 31/00; A61M 29/00; A61M 5/32
(52) U.S. Cl. .................. 604/48; 604/104; 604/105; 604/106; 604/107; 604/174; 604/175; 604/93.01
(58) Field of Search ............................. 604/93.01, 95.04, 604/280, 160, 103, 174–175, 104–107, 48; 128/656, 772

(56) References Cited

U.S. PATENT DOCUMENTS

| | | | | |
|---|---|---|---|---|
| 4,500,313 A | * | 2/1985 | Young | |
| 4,553,959 A | * | 11/1985 | Hickey et al. | 604/96 |
| 4,554,929 A | * | 11/1985 | Samson et al. | |
| 5,255,679 A | | 10/1993 | Imran | |
| 5,318,041 A | * | 6/1994 | DuBois et al. | |
| 5,596,996 A | * | 1/1997 | Johanson et al. | |
| 5,681,280 A | * | 10/1997 | Rusk et al. | |
| 5,749,826 A | * | 5/1998 | Faulkner | 600/29 |
| 6,052,612 A | * | 4/2000 | Desai | |

* cited by examiner

*Primary Examiner*—Timothy L. Maust
*Assistant Examiner*—Anuradha Ramana
(74) *Attorney, Agent, or Firm*—Browdy and Neimark, P.L.L.C.

(57) ABSTRACT

An indwelling catheter comprising a flexible malecot tube having a plurality of slits elongating toward the longitudinal direction in the vicinity of the tip of the catheter, a flexible core wire movable in the axial direction along the malecot tube with its tip fixed to the tip of the malecot tube, a cylindrical connector fixed to the root side of the malecot tube and permitting the root of the core wire to protrude out of the end portion of the malecot tube, and a stopper provided on the connector to constrain arbitrary movement of the core wire.

8 Claims, 5 Drawing Sheets

INDWELLING URETHRA CATHETER

BACKGROUND OF THE INVENTION

1. Field of the Invention

The present invention relates to an indwelling catheter. More particularly, the present invention relates to an indwelling catheter to be used for inserting through the urethra of an animal or human to the bladder in order to facilitate urination, sampling of the urine from inside of the bladder, or administration of medicines into the bladder.

2. Description of the Related Art

Urination becomes difficult when inflammation is caused in the urethra of animals, such as a dog or cat, or a human body. One method for treating such dysuria is to temporarily insert a catheter through the urethra from the outside to secure passageway for urination. The catheter is also used for treating lesions in the bladder.

Figure 7A:
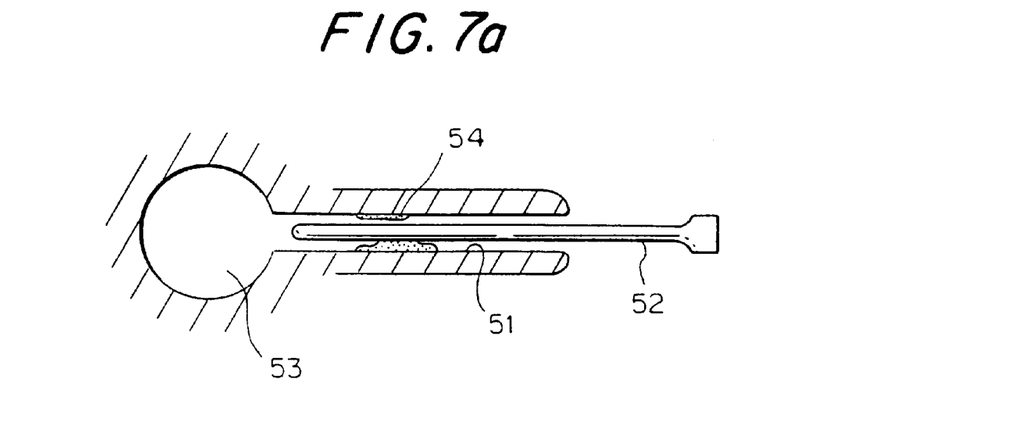
FIG. 7a illustrates a side view of the conventional catheter to be used for an animal.
Figure 7B:
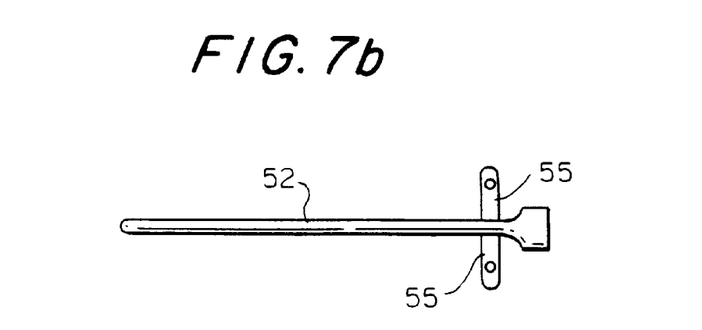
FIG. 7b illustrates a plane view of the conventional catheter to be used for an animal.

FIG. 7a shows the use of a catheter for treating lesions in the bladder of a dog, cat, or the like, wherein the catheter 52 is inserted from the tip of the urethra 51. The reference numerals 53 and 54 denote the bladder and inflammation site caused in the urethra 51. The catheter 52 may be pulled out after the treatment without allowing the catheter 52 to remain in the urethra 51. However, inserting the catheter every time for the treatment may impose a great burden on the animal. Otherwise, the catheter 52 cannot be inserted into the urethra 51 when urethritis is worsened, causing lethal complications that require surgical operation of the abdomen. For countermeasures for such diseases, a stitch margin 55 rovided at both sides of the portion protruding out of the catheter 52 is sewed to the skin in order to permit the catheter 52 to permanently stay in the urethra 51 as shown in FIG. 7b.

Figure 8:
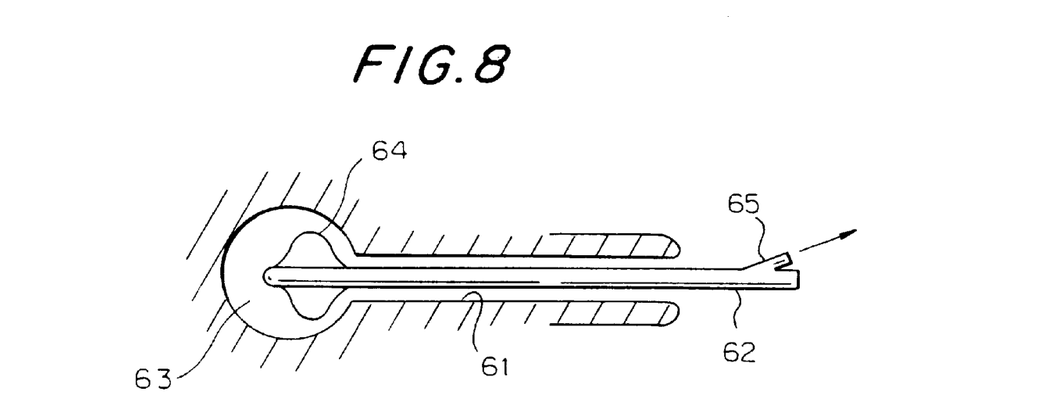
FIG. 8 illustrates a conventional indwelling catheter for the human body.

In the case of therapy for a human body, on the other hand, a catheter 62 having a balloon at the tip (balloon catheter) is placed in the urethra 61 as shown in FIG. 8. The reference numeral 63 in the drawing denotes the bladder 63. The tip of the catheter 62 has a elastically expandable and contractible balloon 64, and the catheter 62 also has a branched ventilation hole 65 at the other end. The balloon 64 inserted into the bladder 63 is inflated by sending air from the ventilation hole 65, and retained there by closing the ventilation hole 65 so that the catheter 62 is not pulled out of the urethra 61. When the catheter 62 is pulled out of the urethra 61, air is released by opening the ventilation hole 65 to allow the balloon 64 to contract taking advantage of its elasticity.

A potential catheter for measuring electrocardiograph has been proposed in FIG. 7 of U.S. Pat. No. 5,255,679, wherein a basket having vertical slits is provided in the vicinity at the tip of the tube, the tip of the core wire passing through the inside of the tube is bonded to the tip of the tube, and the basket disposing a number of electrodes is expanded by pulling in and out the core wire.

However, it is difficult to retain the catheter 52 for a long period of time when the stitch margin 55 of the catheter 52 is sewed to the skin of the animal for treating the animal, giving great stress to the animal. When the animal is a male, the penis should be exposed from the foreskin to dry the mucous membrane or to induce other inflammations which require incision of the abdomen or lead the animal to death. While the balloon catheter 62 is not required to be sewed to the skin, on the other hand, the balloon 64 may fail to contract by opening the ventilation hole 65 when, for example, urine components are accumulated on the surface of the balloon 64 to compromise elasticity of the balloon. An operation for forcibly breaking the balloon 64 from under the abdominal cavity is required when the balloon does not contract.

SUMMARY OF THE INVENTION

Accordingly, it is an object of the present invention for solving the foregoing problems to provide an indwelling catheter that is not required to be sewed to the skin and is able to retain it in the urethra by a single operation, besides it is easily pulled out of the urethra.

An indwelling catheter according to the present invention comprises a flexible malecot tube having a plurality of slits elongating in the longitudinal direction in the vicinity of the tip of the catheter, a flexible core wire disposed to be freely movable in the axial direction along the malecot tube with its tip fixed to the tip of the malecot tube, a cylindrical connector fixed to the root side of the malecot tube into which the root area of the core wire is inserted, and a stopper provided on the connector in order to constrain arbitrary movement of the core wire.

While the indwelling catheter as described above may have an another passageway different from the flow passageway for permitting a liquid in the malecot tube to flow through, and the core wire may be housed in the former passageway, the core wire is preferably housed in the flow passageway within the malecot tube with remaining a marginal space for allowing the liquid to flow through the flow passageway. The stopper is preferably a rubber member having a hole for allowing the core wire to penetrate so that the rubber member is capable of constraining motion of the core wire by frictional force, and exerting a seal function between the core wire and the connector. Alternatively, the stopper may comprise a member provided on the connector and mechanically engaging with the core wire. An opening for communicating between the inside and outside of the connector and a sealing lid for freely opening and shutting the opening are preferably provided on the side wall of the connector.

The tip of the malecot tube preferably has a member for confirming insertion margin such as an imaging member or a scale or a graduation. More preferably, a knob is attached at the root of the core wire protruding out of the end face of the connector, and the core wire has a snap-off portion for snapping the core wire with some remaining sites protruding out of the end face of the connector when the core wire is pulled out of the root side of connector. The indwelling catheter according to the present invention preferably has a cover for covering the end portion of the remaining snapped core wire on the end face of the connector. More preferably, the root area of the core wire is previously separated into the tip side and root side and these end portions of the separated core wire are connected with a snap-off tube into which both end portions are inserted. A snap point that can be readily snapped is formed at a site a distance shifted from the junction of two core wires in the snap-off tube.

In the indwelling catheter according to the present invention, when the root of the core wire protruding out of the end portion of the connector is pulled with one hand while holding the connector with the other hand, a compression force is applied to the malecot tube, because the tip of the core wire is fixed to the malecot tube. Consequently, tape-shaped sites divided by the slit on the malecot tube are buckled and outwardly expanded by being bent at the center of the tape. The bent configuration is maintained by the action of the stopper. When the root of the core wire is pushed in the tip side, a tensile force is applied to the malecot tube to expand the tape-shaped site and the malecot portion is contracted.

Accordingly, a simple operation is sufficient for retaining the catheter in the urethra, wherein the malecot tube is at first inserted into the urethra until the tip of the malecot tube is enveloped in the bladder, then the malecot part is expanded by pulling the core wire followed by allowing the stopper to operate. This procedure permit the expanded malecot part to be maintained, and the inner wall of the bladder catches the expanded malecot part to securely retain the catheter in the urethra. Labor of a treatable operator is reduced and stress on an animal such as a dog or cat may be alleviated by the process as described above. The main body of the catheter can be gently retained in the body, thereby enabling the therapy period to be reduced and therapeutic ratio to be improved.

Since only the connector portion of the catheter is exposed out of the urethra, the animal neither bites nor licks the connector of the catheter to pull out the catheter. For pulling out the catheter, the expanded malecot portion can be forcibly contracted by pushing the core wire, thereby the catheter can be readily pulled out of the urethra by pulling the contracted catheter.

In the indwelling catheter in which the core tube is housed with a marginal space for allowing the liquid to flow through the malecot tube, the catheter is not particularly required to have a large inner diameter since the flow passage serves as a space for allowing a liquid to flow through and a passageway for inserting the core wire. Instead, the catheter has an approximately the same diameter as conventional catheters. Further, since the catheter has only one inner space, the catheter has a simple construction to be easily manufactured.

In the indwelling catheter in which the catheter in which the stopper is a rubber member having a hole for allowing the core wire to penetrate therethrough in order to seal between the core wire and the connector, motion of the core wire in the axial direction can be constrained by elasticity and frictional resistance of the rubber member. Consequently, intended movement of the core wire can be made easy while reducing the possibility of unintended or arbitrary movement of the core wire. Accordingly, the malecot tube can be easily expanded and contracted with few possibilities of falling down of the indwelling catheter from the urethra as a result of arbitrary expansion of the malecot tube. The stopper has a simple construction and is easily manufactured, since the stopper is merely composed of the rubber member. Another seal member need not be separately provided because the rubber member exerts a seal function between the connector and the core wire. The seal function by the rubber member also prevents invasion of microorganisms from the outside while the catheter is retained. Retention of the indwelling catheter is further secured when the stopper comprises a member mechanically engaging the core wire provided in the connector.

In the indwelling catheter having an opening for communicating between the outside and inside of the side wall of the connector and a sealing lid for freely opening and shutting the opening, sampling of urine and injection of therapeutic agents may be facilitated via the opening. In addition, invasion of microorganisms can be also prevented since the opening can be sealed with the lid while retaining the catheter.

In the indwelling catheter having a member for confirming insertion margin at the tip of the malecot tube, the malecot can be expanded after completely confirming that the malecot portion has been enveloped in the bladder. In the indwelling catheter having a knob attached at the root of the core wire protruding out of the end portion of the connector, wherein the core wire has a snap-off portion for snapping the core wire with some remaining sites protruding out of the end face of the connector when the core wire is pulled out of the root side of connector, the core wire can be easily pulled out of the connector by pulling the knob. Excess protruding portions of the knob and core wire may be easily removed since the core wire can be readily snapped at the snap portion after pulling out the core wire, thereby the animals may hardly bite or lick the knob. The malecot portion of the indwelling catheter that has been once pulled out cannot be expanded again by snapping the core wire at the snap site, thereby possibilities of secondary infection can be eliminated to ensure perfect disposable use of the catheter. In the indwelling catheter having a cover for covering the end portion of the remaining snapped core wire on the end face of the connector, the root of the core wire is protected from being licked by the animal since the root of the core wire is covered with the cover, or the root never damages the skin of the animal.

In the indwelling catheter in which the root area of the core wire is previously separated into the tip side and the root side and these end portions are connected with a snap-off tube into which both end portions are inserted, and in which a snap point readily snapped is formed at a site a distance shifted from the junction of two core wires in the snap-off tube, the snap-off tube is broken at the snap point when a force is applied to the root of the core wire in a bending direction, thereby the core wire can be easily separated into the tip side and root side. In addition, since the site where the core wire is separated is shifted from the snap point of the snap-off tube, the core tube protruding out of the broken part of the snap-off tube can be inserted into the cavity of the other snap-off tube. Accordingly, the root side of the core wire attached with the knob once separated may be temporarily connected to the end portion at the tip side to push the core wire toward the tip side using the knob. The malecot portion can be readily contracted by the operation described above.

BRIEF DESCRIPTION OF THE DRAWINGS

FIG. 4b is an enlarged cross section of the core wire of the connector shown in FIG. 4a;

FIG. 5b is a cross section along the line V—V of the core wire shown in FIG. 4a;

FIG. 5c is a cross section along the line V—V of the core wire shown in FIG. 4a;

FIG. 6b is a cross section along the line V—V of the malecot tube shown in FIG. 6a;

DESCRIPTION OF THE PREFERRED EMBODIMENTS

Embodiments of the indwelling catheter according to the present invention will be described with reference to the drawings.

Figure 3:
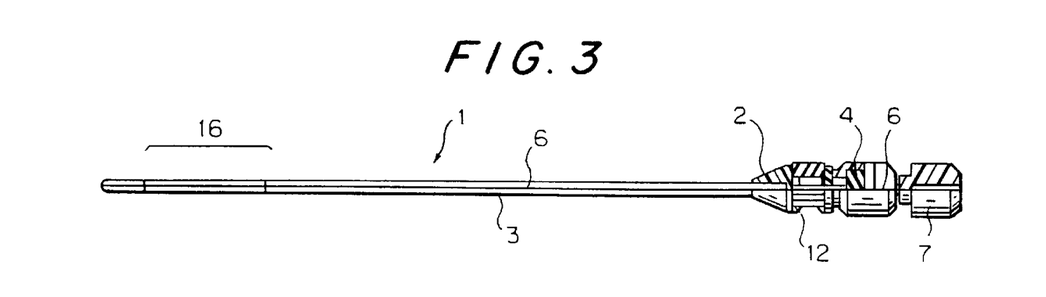
FIG. 3 is a partial cross sectional side view of one embodiment of the catheter according to the present invention.
Figure 4A:
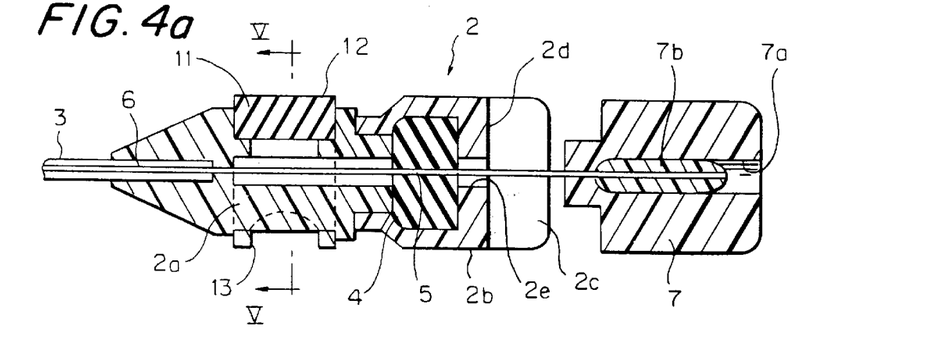
FIG. 4a is an enlarged vertical cross section of the main part in the vicinity of the connector of the catheter shown in FIG. 3.

The base side (the right side of the drawing) of the catheter 1 shown in FIG. 3 has a connector 2, and the base of a flexible malecot tube 3 is fixed at the tip of the connector. The connector 2, as shown in FIG. 4, substantially has a cylindrical shape and made of a molded synthetic resin such as a transparent acrylic resin. The interior of the connector 2 forms a cavity, and small holes are perforated at both ends along the axis direction. The tip side of the connector 2 is formed into an approximate conical shape, where the base of the malecot tube 3 is embedded and bonded. The malecot tube 3 is made of, for example, a transparent polyurethane resin.

A round column of a rubber seal 4 is attached within the connector 2 as a stopper, and a penetration hole 5 penetrating from the front to the rear is formed or drilled at the center of the rubber seal 4. The connector 2 is formed into two parts, one is a front part 2a and the other is a cylindrical rear part 2b having a bottom seal, in order to house the rubber seal 4 in the connector 2. The rear part 2b is fused to and integrated with the front part 2a by, for example, heat molding of the front end of the rear part after attaching the rubber seal 4 in the connector. The two parts may be fitted with screws, or may be adhered with adhesives to each another. The rubber seal 4 may be made of natural rubber, for example. A flexible core wire 6 is inserted into the penetration hole 5 of the rubber seal 4 and the malecot tube 3 to be freely movable along the axis direction. The core wire 6 may be formed of, for example, a stainless steel wire. A groove or slit 2d is formed at the rear end of the connector 2 in order to form a cover 2c for covering the end portion of the snapped core wire 6.

Figure 4B:
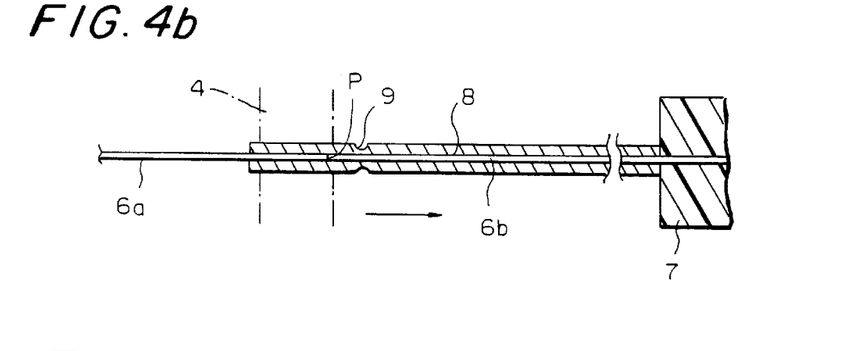
Figure 4C:
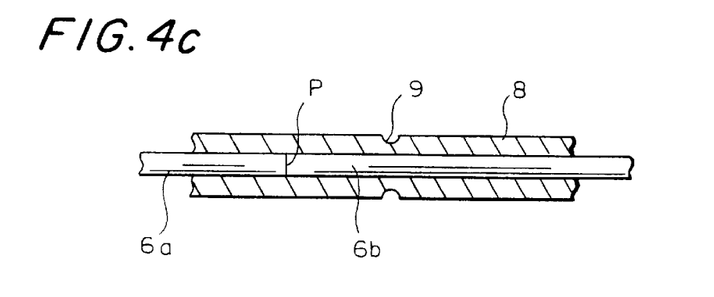
FIG. 4c is an enlarged cross section of the main part of the core wire shown in FIG. 4b.

The base portion of the core wire 6 protrudes out of a hole 2e at the rear end of the connector 2, and a knob 7 having an approximately cylindrical shape is fixed at the end of the core wire. An engage hole 7a is formed in the knob 7, and engages the core wire by inserting an engage piece or anchor 7b fixed to the root of the core wire 6 in this embodiment. As shown in the enlarged drawing FIG. 4b, the core wire 6 is divided into a front side 6a and base side 6b at a separation point P, and the front side and base side are connected to each other with a snap-off tube 8 formed around them. In other words, the front side 6a is fixed to the front portion of the snap-off tube 8, and the base side 6b is fixed to the rear portion of the snap-off tube 8. The snap-off tube 8 may be made of, for example, a stainless steel pipe. As shown in FIG. 4c, a snap point 9 that has an annular groove and can be easily snapped is formed around the snap-off tube 8. While the snap point 9 is provided at the position a little shifted from the separation point P of the core wire 6, it may be shifted toward the tip side.

The outer diameter of the snap-off tube 8 is adjusted to be a little smaller than the inner diameter of the penetration hole 5 of the rubber seal 4, so that the core wire 6 can freely slide relative to the penetration hole 5 of the rubber seal 4, and the inner circumference face of the penetration hole 5 of the rubber seal 4 presses the outer circumference face of the core wire 6. This arrangement enables the core wire 6 to move along the axis line when a certain magnitude or more of force is applied, besides preventing arbitrary movement of the core wire 6 by frictional force between the core wire and the rubber seal. The core wire can be willingly moved or stopped at a desired position. In addition, invasion of microorganisms through the gap between the core wire 6 and the connector 2 can be also prevented.

With reference to FIG. 4a again, an opening 10 for communicating the inner cavity to the outside is provided in front of the connector 2. An annular groove 11 is also formed on the outer circumference face of the connector 2 at the portion corresponding to the opening 10, and a rubber ring 12 made of natural rubber is fitted into the annular groove 11. The upper part of the groove 11 is flattened as shown in FIG. 5c to make the corresponding part of the rubber ring 12 to have a larger thickness than the remaining part. Consequently, arbitrary rotation of the rubber ring 12 is prevented. A window 13 is formed at the lower part of the rubber ring 12. This rubber ring 12 closes the opening 10 when the window 13 rotates to the downward as shown in FIG. 4a, and opens the opening 10 of the connector 2 when the window 13 rotates to the upward. Therefore, this rubber ring 12 functions as a lid according to claim 4.

Figure 5A:
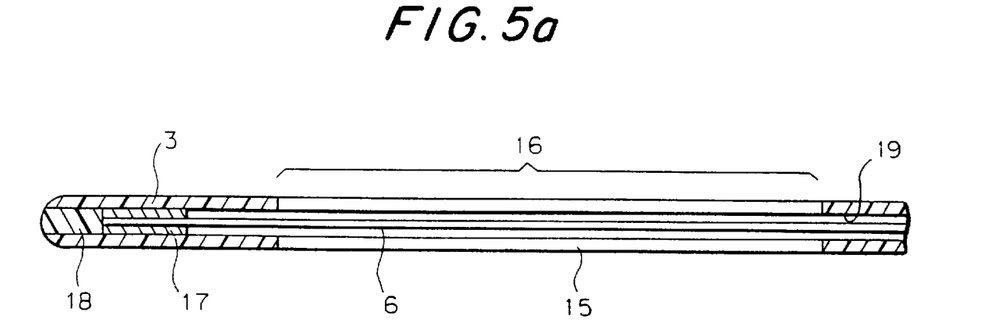
FIG. 5a is an enlarged cross section of the main part of the tip of the catheter and the malecot tube shown in FIG. 3.
Figure 5B:
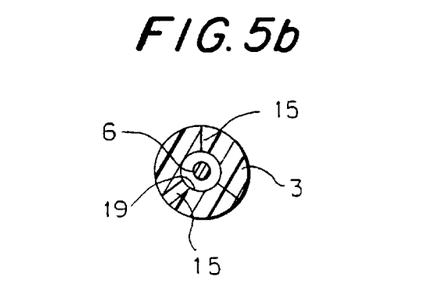
Figure 5C:
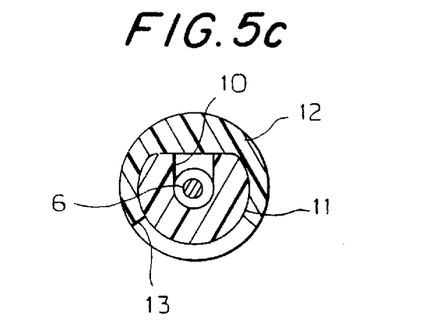

Slits 15 are cut at the tip side of the malecot tube 3 along the axial direction as shown in FIG. 5a. As shown in FIG. 5b, three slits 15 are formed with an approximately equal distance to each other along the circumference direction of the malecot tube 3. These slitted portion of the malecot tube is the malecot portion 16. While the length of the slit 15 may be appropriately selected depending on the outer diameter and length of the malecot tube 3, the length of the slit 15 is about 20 mm when the malecot tube has an outer diameter of about 1.5 mm and a length of about 115 mm. The slit 15 usually has no appreciable width since it is formed by cutting. However, the slit 15 may have some degree of width. A tubular chip 17 made of stainless steel is fixed to the tip of the core wire 6, and the outer circumference face of the chip 17 is adhered to the inner circumference face in the vicinity of the tip of the malecot tube 3 with an epoxy based adhesive. The adhesive 18 is also filled in the open space at the tip of the malecot tube 3, thereby the tip portion of the core wire 6 is fixed at the site close to the tip of malecot tube 3. The tip of the cured adhesive 18 is rounded by grinding in order to protect the urethra during insertion of the catheter.

Figure 1:
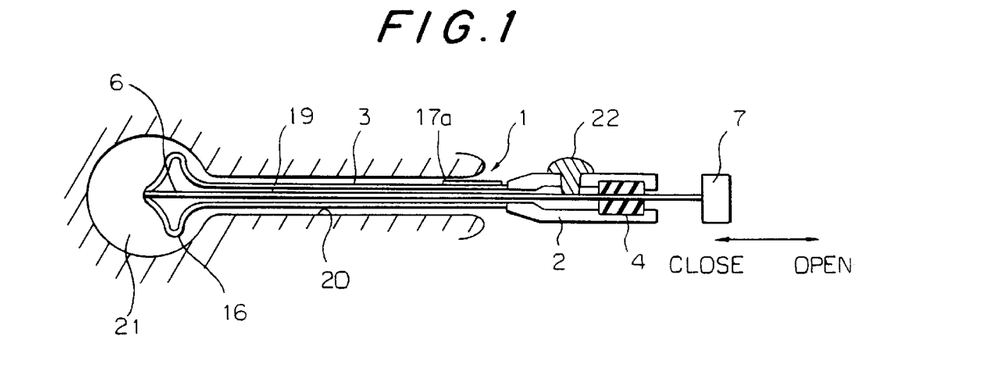
FIG. 1 is a side view showing operation of the catheter according to the present invention.

Since the stainless steel chip 17 as well as the stainless steel core wire 6 are permeable to X-ray, they cannot be used as imaging members. However, a high image forming function can be obtained when the chip 17 to be covered on the core wire 6 is made of platinum, tungsten or gold. A coil may covered the core wire 6 in place of the chip 17. The malecot tube 3 itself can be endowed with an image forming function by using a mixture of imaging powders such as barium sulfate or bismuth bicarbonate as a material of the malecot tube 3 at the tip of the tube or over the entire length of the tube. When the indwelling catheter is inserted into the urethra, the position of the chip 17 in the bladder can be confirmed using X-ray and the malecot portion can be expanded after confirming that the malecot portion is completely enveloped in the bladder by endowing the indwelling catheter with an imaging function. The approximate position of the tip of the malecot tube 3 when the catheter is inserted into the urethra as shown in FIG. 1 can be visualized by printing a scale (graduation) 17a on the malecot tube 3. The imaging member such as the chip 17 or the scale 17a correspond to the member for confirming the insertion margin according to the present invention.

The outer diameter of the core tube 6 is adjusted to be smaller than the inner diameter of the malecot tube 3. As a result, a space 19 is provided between the inner circumference face of the malecot tube 3 and the core tube 6 as shown in FIG. 5b. This space 19 is continuously formed from the tip side of the malecot tube 3 to the cavity in the connector 2. This space 19 functions as the passageway for sampling of the urine or administration of a medicine by the catheter 1. In other words, the inner cavity of the malecot tube 3 functions as both the passageway for inserting the core wire 6 and flow path for liquids.

Figure 6A:
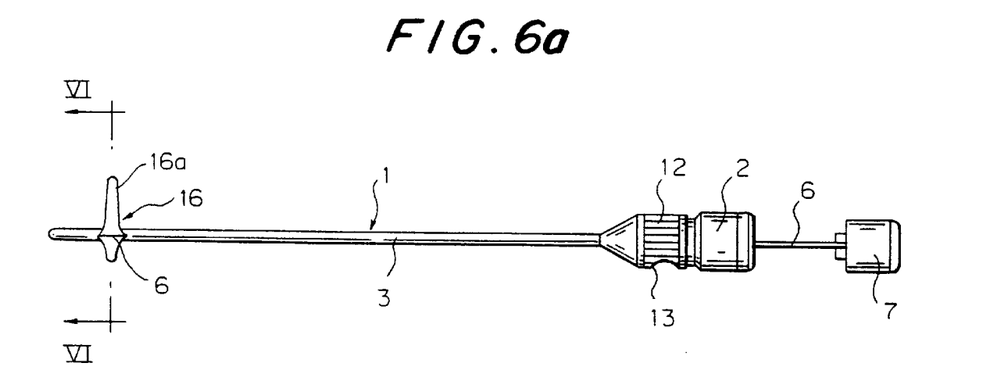
FIG. 6a is a side view of the expanded malecot tube of the catheter shown in FIG. 3.
Figure 6B:
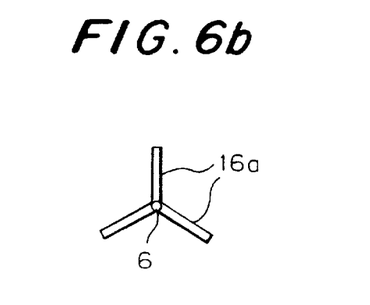

For operating the catheter 1 having the construction as described above, the connector 2 is held with fingers of one hand and the knob 7 is held and pulled with fingers of the other hand to cooperatively slide the core wire 6 toward the front side. The same movement of the core wire is possible by pushing the hand holding the connector 2 while the hand holding the knob 7 remains stationary. The tip of the malecot tube 3 is also pulled toward the operator's front side by pulling the core wire 6 toward the front side to apply a compression force to the tube. As a consequence, three tape-shaped portions 16a constituting the malecot portion 16 buckle to permit the malecot portion 16 to expand as shown in FIGS. 6a and 6b. The core wire 6 is maintained in the proper site by the frictional force of the rubber seal 4 as described above, when the knob 7 is released from the hand while the malecot portion 16 is expanding. The same operation as described above is possible when the malecot tube 3 and the core wire 6 are smoothly curved.

Figure 4D:
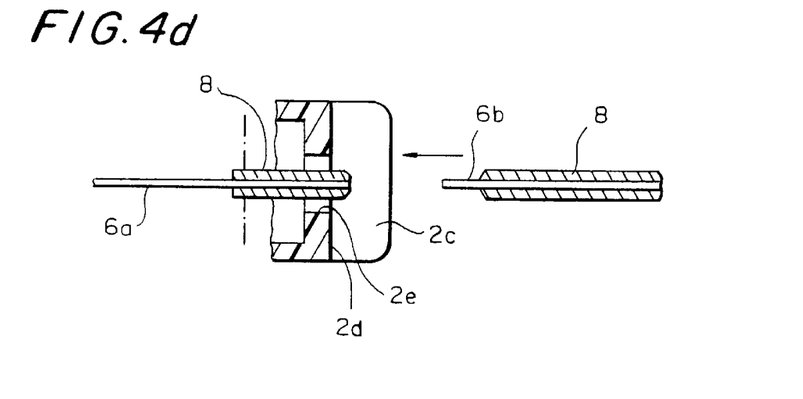
FIG. 4d is a cross section showing separation of the core wire shown in FIG. 4b.

The snap-off tube 8 is exposed from the penetration hole 5 of the connector 2 as shown in FIG. 4b by pulling the core wire 6 out of the connector 2. The snap-off tube is snapped at the snap point. As shown in FIG. 4d, the remaining portion of the snapped tube remains to be exposed from the penetration hole 5 of the connector 2. However, the portion is not an obstacle since it is hidden in the groove 2d between the cover portions 2c. The catheter 1 is retained as the snapped tube is remaining. The knob 7, core wire 6b and snap-off tube 8 remaining at the snapped side are stored. As shown in FIG. 4d, the end portion of the core wire 6 is a little retired from the end portion of the snap-off tube 8.

When the catheter 1 is taken away, the stored knob 7 is held, the tip of the core wire 6b at the snapped side is fitted to the end portion of the remaining snap-off tube 8 and the end faces of the core wires 6a and 6b are made to contact to each other. Then, the knob 7 is pushed to slide the entire core wires 6a and 6b toward the tip end side of the malecot tube 3, thereby returning the malecot portion 16 to its original state as shown in FIG. 3. This operation for returning the malecot portion is also possible when the malecot tube 3 and the core wire 6 are smoothly curved.

The therapeutic method performed by actually inserting the catheter 1 into the urethra of an animal such as a dog or cat, or of a human will be described hereinafter. The catheter 1 before inflating the malecot portion 16 is at first inserted from the tip of the urethra 20 in FIG. 1 to position the tip of the malecot portion 16 in the bladder 21. Next, the knob 7 is pulled toward the operator's front side to allow the core wire 6 to slide toward the front side, thereby the malecot portion 16 inside of the bladder 21 is expanded. The malecot portion 16 can be prevented from being pulled out of the bladder 21 since the expanded malecot portion 16 serves as a stopper, thereby the catheter 1 is retained in the bladder.

Figure 2:
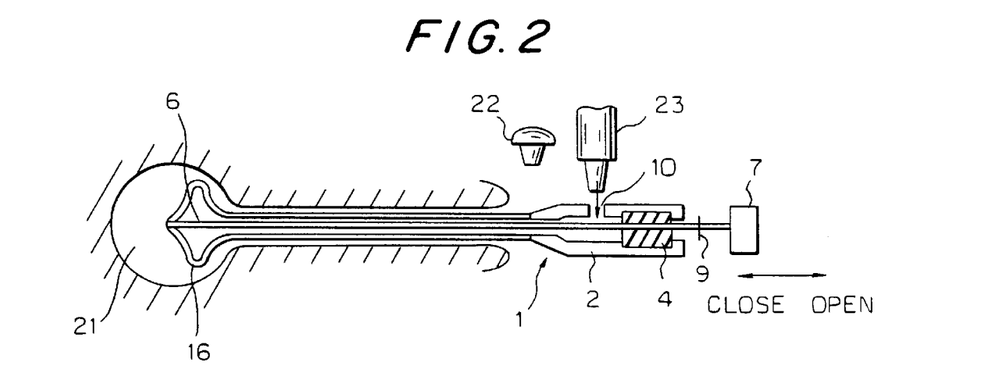
FIG. 2 is a side view showing operation of the catheter according to the present invention.

Various therapies can be applied while the catheter 1 is retaining. For example, the lid or plug 22 is removed from the connector 2, a urine sampler 23 is fitted to the opening 10 of the connector 2, and the urine in the bladder 21 is sampled via the flow passage or space 19 of the catheter 1 as shown in FIG. 2. Otherwise, a therapeutic agent can be injected into the bladder 21 from the opening 10 of the connector 2 via the flow passage 19.

The malecot portion 16 can be contracted by pushing the core wire 6 toward the tip side for removing the catheter 1 after completing the therapy. Consequently, the catheter 1 can be readily pulled out of the urethra 20 by pulling the catheter 1 with the contracted malecot portion 16 toward the front side.

As hitherto described, the catheter 1 can be retained in the bladder 21 or urethra 20 through one touch operation merely by inserting the catheter 1 into the urethra 20 and pulling the knob 7 toward the front side. Accordingly, the therapeutic period may be shortened and therapeutic ratio may be improved. Labor of treatable operators is reduced and stress on the animal may be alleviated since the catheter 1 can be more readily retained as compared with the conventional method. It is also easy to pull the catheter 1 out of the urethra 20. Since the knob 7 is separated at the snap portion, the core wire 6a cannot be pulled again, completely ensuring disposable use of the catheter.

Frictional force of the rubber seal 4 is utilized for holding the core wire 6 at a proper position in the embodiment as hitherto described. Consequently, the penetration hole 5 of the rubber seal 4 ensures complete sealing to prevent microorganisms from invading into the urethra while the catheter 1 is retained.

A snap point may be directly provided on the core wire 6 without using any snap-off tube 8 for making the construction of the catheter simple. The core wire 6 may be snapped or bent using a tool. However, it is preferable for simple operation to provide a snap-off tube 8 or snap point 9. For the snap point of the snap-off tube 8 or core wire 6, the end portions of the previously separated snap-off tubes or core wires may be bonded to each other with an adhesive capable of snapping. Providing the snap-off tube 8 gives an advantage of stabilizing frictional force by the rubber seal, since the diameter of the core wire 6 increases at the snap point.

When the frictional force between the snap-off tube or the core wire and the rubber seal is insufficient for preventing displacement of the core wire, on the other hand, a stopper mechanism comprising, for example, the core wire and a collet chuck may be provided. This stopper mechanism is composed of a connector, core wire, collet chuck and tightening nut.

What is claimed is:

1. An indwelling urethra catheter comprising;
   a flexible malecot tube having a plurality of slits elongating toward the longitudinal direction in the vicinity of the tip of the catheter;
   a flexible core wire disposed within said tube movable in the axial direction along the malecot tube with its tip fixed to the tip of the malecot tube;
   a cylindrical connector fixed to the root side of the malecot tube and permitting the root of the core wire to protrude out of the end portion of the malecot tube; and
   a stopper provided on the connector to constrain arbitrary movement of the core wire, wherein said core wire is housed in a flow passage for liquid to flow therethrough within the malecot tube with a marginal space between the core wire and the tube interior.

2. The indwelling urethra catheter according to claim 1, wherein said stopper is a member provided on the connector and being mechanically engageable with the core wire.

3. The indwelling urethra catheter according to claim 1, wherein said malecot tube has means for confirming insertion margin.

4. An indwelling urethra catheter comprising:

a flexible malecot tube having a plurality of slits elongating toward the longitudinal direction in the vicinity of the tip of the catheter;

a flexible core wire disposed within said tube movably in the axial direction along the malecot tube with its tip fixed to the tip of the malecot tube;

a cylindrical connector fixed to the root side of the malecot tube and permitting the root of the core wire to protrude out of the end portion of the malecote tube;

and a stopper provided on the connector to constrain arbitrary movement of the core wire, wherein said core wire is housed in a flow passageway for liquid to flow therethrough within the malecot tube with a marginal space between the core wire and the tube interior;

said stopper is a rubber member having a hole for allowing the core wire to penetrate;

and said rubber member is capable of constraining movement of the core wire by frictional force, and of exerting a seal function between the core wire and the connector.

5. An indwelling urethra catheter comprising:

a flexible malecot tube having a plurality of slits elongating toward the longitudinal direction in the vicinity of the tip of the catheter;

a flexible core wire disposed within said tube movably in the axial direction along the malecot tube with its tip fixed to the tip of the malecot tube;

a cylindrical connector fixed to the root side of the malecot tube and permitting the root of the core wire to protrude out of the end portion of the malecot tube;

a stopper provided on the connector to constrain arbitrary movement of the core wire, wherein said core wire is housed in a flow passageway for liquid to flow therethrough within the malecot tube with a marginal space between the core wire and the tube interior; and wherein an opening for communication between the inside and outside of the said connector and a sealing lid for freely opening and shutting the opening are provided on the side wall of said connector.

6. An indwelling urethra catheter comprising:

a flexible malecot tube having a plurality of slits elongating toward the longitudinal direction in the vicinity of the tip of the catheter;

a flexible core wire disposed within said tube movably in the axial direction along the malecot tube with its tip fixed to the tip of the malecot tube;

a cylindrical connector fixed to the root side of the malecot tube and permitting the root of the core wire to protrude out of the end portion of the malecot tube;

a stopper provided on the connector to constrain arbitrary movement of the core wire, wherein said core wire is housed in a flow passageway for liquid to flow therethrough within the malecot tube with a marginal space between the core wire and the tube interior; and a knob is attached at the root of the core wire protruding out of the end portion of said connector, and said core wire has a separation point for snapping the core wire and a separated portion protrudes out of the end face of said connector from inside of the end face of said connector, when said core wire is pulled out of said connector.

7. The indwelling urethra catheter according to claim 6 having a cover for covering the end portion of the remaining snapped core wire in the end face of said connector.

8. The indwelling urethra catheter according to claim 6, wherein the root area of the said core wire is previously separated into the tip end side and the root side and these end portions are connected with a snap off tube into which both end portions are inserted, and a snap point that can be readily snapped is formed at a site a distance shifted from the junction of two core wires in the snap-off tube.

* * * * *